United States Patent
Lin et al.

(10) Patent No.: US 6,712,503 B2
(45) Date of Patent: Mar. 30, 2004

(54) METHOD TO CALCULATE FUEL DI NUMBER FROM A MEASURED CURVE

(75) Inventors: Yingjie Lin, El Paso, TX (US); Han-Sheng Lee, Bloomfield Hills, MI (US); Su-Chee Simon Wang, Troy, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 10/117,833

(22) Filed: Apr. 8, 2002

(65) Prior Publication Data

US 2003/0189969 A1 Oct. 9, 2003

(51) Int. Cl.$^7$ ................................................ G01N 25/00

(52) U.S. Cl. ............................ 374/45; 374/43; 374/144

(58) Field of Search .................. 374/1, 45, 54, 374/184, 163, 159, 43, 144

(56) References Cited

U.S. PATENT DOCUMENTS

| | | | | |
|---|---|---|---|---|
| 5,225,679 A | * | 7/1993 | Clarke et al. | 250/343 |
| 5,569,922 A | * | 10/1996 | Clarke | 250/339.12 |
| 5,750,995 A | * | 5/1998 | Clarke | 250/339.12 |
| 5,949,695 A | * | 9/1999 | Snell | 708/290 |
| 6,295,808 B1 | * | 10/2001 | Griffin et al. | 60/776 |
| 6,360,587 B1 | | 3/2002 | Noel | |
| 6,360,726 B1 | * | 3/2002 | Javaherian | 123/491 |
| 6,520,166 B1 | | 2/2003 | Karau et al. | |

OTHER PUBLICATIONS

U.S. patent application Publication, Feb. 2003, Lambert et al.*
Standard Method of Test For Distillation of Petroleum Products, D86–82, Institute of Petroleum, London, "Standard Methods for Analysis and Testing of Petroleum and Related Products 1991", vol. 1, Methods IP1–280, pp. 123.1–123.14.*
Standard Test Method for Distillation of Petroleum Products at Atmospheric Pressure, Designation D86–97, ASTM, no date.*

* cited by examiner

*Primary Examiner*—Diego Gutierrez
*Assistant Examiner*—Lydia M. DeJesús
(74) *Attorney, Agent, or Firm*—Jimmy L. Funke

(57) ABSTRACT

A method to calculate a fuel driveability index (DI) value is provided from a sample of fuel in a container as tested by the industry standard ASTM D86 test providing particular temperature data at various percentages of evaporation as the container is heated. The particular temperature data provides a DI value. The same sample of fuel is tested on a sensor capable of retaining a predetermined volume of fuel. Temperature data is monitored at the same percentages of evaporation as the sensor is being heated. Correlation equations are mathematically calculated between the temperature data from the sensor relative to the particular temperature data from the ASTM D86 test and stored in the engine controller of a vehicle. The fuel from the fuel tank is tested by heating a similar on-board sensor having the predetermined volume of fuel and measuring the temperature data as a function of the remaining fuel in the sensor. The stored correlation equations are applied to the measured temperatures to provide the required temperature data to calculate the DI value for the fuel in the fuel tank.

14 Claims, 3 Drawing Sheets

METHOD TO CALCULATE FUEL DI NUMBER FROM A MEASURED CURVE

FIELD OF THE INVENTION

This invention relates to an on-board sensing element and method for using the same to measure the volatility of a sample of non-ethanol gasoline by measuring the change in capacitance of the sensing element as a function of time and temperature and using the measurements to estimate the driveability index (DI) of the sample.

BACKGROUND OF THE INVENTION

It is known in the art relating to automotive engines, that the key gasoline characteristic of good driveability is volatility. Volatility is especially important at the time an engine is started because liquid gasoline must evaporate and mix with air to form a combustible mixture. If too little gasoline is added, the engine will not start. If gasoline beyond that needed to initiate combustion is added, then extra hydrocarbons from an unburned portion of the gasoline are found in the exhaust. Moreover, because gasoline sold in the United States varies in volatility, there is a tradeoff in engine design between low hydrocarbon emissions and good driveability with low volatility fuel.

To describe the effect of gasoline volatility on the cold start and warmup driveability of a vehicle, a driveability index (DI) has been developed. For gasoline that does not contain oxygenates such as ethanol or methyl tertiary-butyl ether (MTBE), the definition of DI is based on a laboratory test (ASTM D86) in which a sample of gasoline is distilled as its temperature is raised. The fraction distilled is measured as a function of temperature and the equation:

$$DI = 1.5T_{10} + 3T_{50} + T_{90}$$

where $T_x$ is the temperature in degrees Fahrenheit at which x % of the gasoline sample has been distilled.

One known way to estimate DI is by measuring the fuels infra-red transmission spectrum. While this approach has proven useful in refineries where the feedstocks are known, it has not been accepted as an accurate way to characterize the DI of finished gasoline in the field.

It is particularly desirable to estimate DI on-board a vehicle. To provide customer satisfaction, engines are calibrated to reliably start with fuel of the lowest volatility. This is done by increasing the amount of fuel in the air/fuel mixture. Consequently, for most starts, the engines air/fuel ratio is richer than optimum. Some of this extra gasoline passes unburned into the exhaust. This is particularly detrimental at the time of a cold start because the catalytic converter is too cold to be active. The added hydrocarbon concentration is typically emitted to the environment.

Estimating DI on-board would permit the air/fuel ratio to be more precisely controlled. The engine would be calibrated to reliably start while extra fuel would only be added when needed to compensate for fuel volatility. On the average, less fuel would be used for cold starts resulting in a decrease in fleet average exhaust hydrocarbon emissions. This decrease in air pollution is an important environmental benefit.

SUMMARY OF THE INVENTION

The present invention provides a method for using an on-board sensor having a sensing element for calculating the fuel DI number from measured changes in electrical capacitance, which is representative of the volume of the fuel filled sensing element as the sensing element is heated to evaporate the fuel within it. Both the heated sensing unit and the standardized test (ASTM D86) measure fuel distillation or vaporization. However, due to different thermal mass and structure of the two systems, measured distillation curves are quite different. Since the ASTM D86 test is the industrial standard, it is necessary to calibrate the measured results from the heated sensing element to match the results obtained from the industrial standard.

Fuel samples are provided to measure the driveability index (DI). Each fuel sample is divided into two containers. One container is used for the ASTM D86 measurements and the other container is used to fill the sensing element for the sensor measurements. The required temperature information is obtained from the D86 measurements to calculate the DI number.

The sensing element is then heated in a controlled environment so that the sensor's change in capacitance and temperature over time is measured. Using mathematical analysis, the relationship of the sensing element data with the standard D86 test data is calibrated to provide correlation measurements. The correlation measurements are stored to the engine controller of the vehicle, which calculates DI as needed. The calculated value of DI is stored for the next cold start where it may be used for setting the desired air/fuel ratio at the time of starting.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

Figure 1:
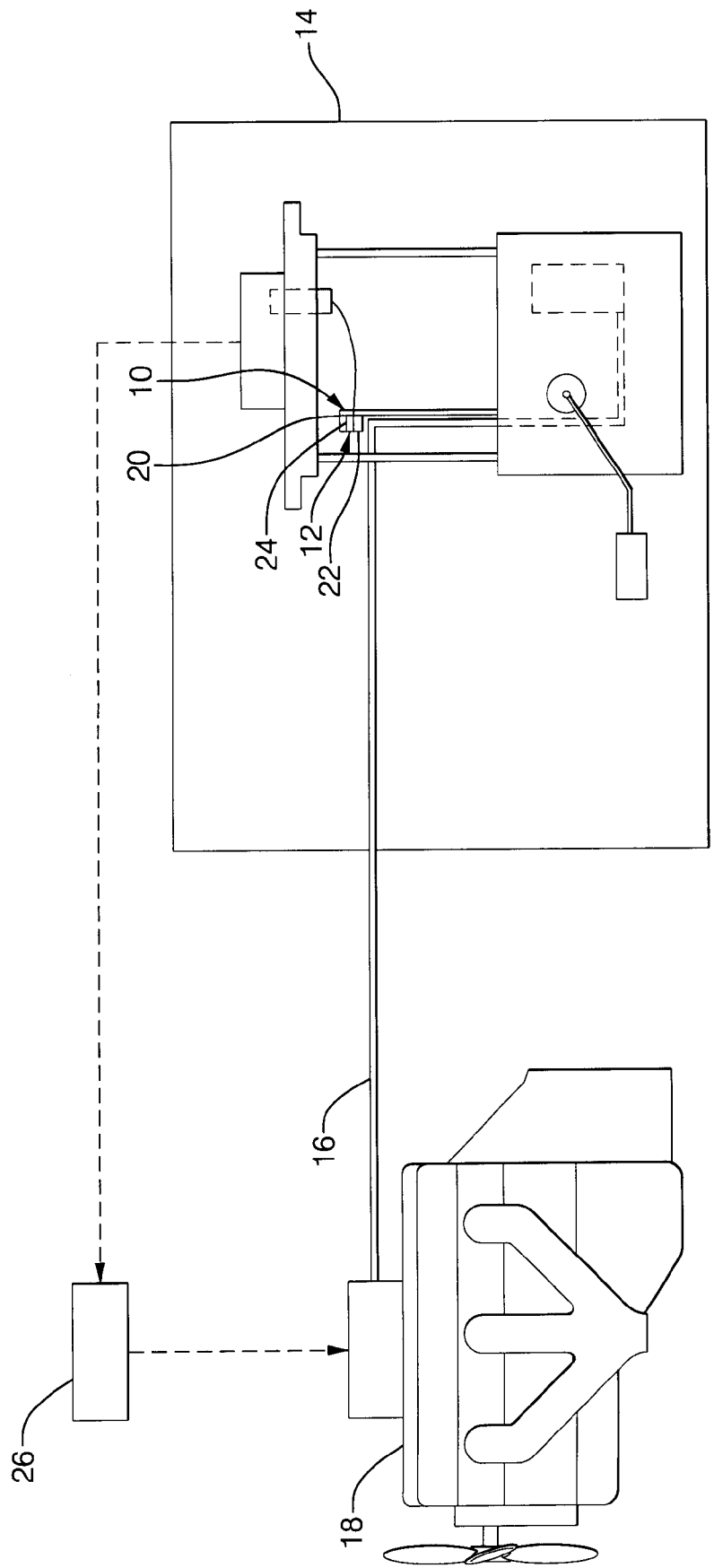
FIG. 1 is a schematic diagram of a fuel system having a sensor for calculating the driveability index.
Figure 2:
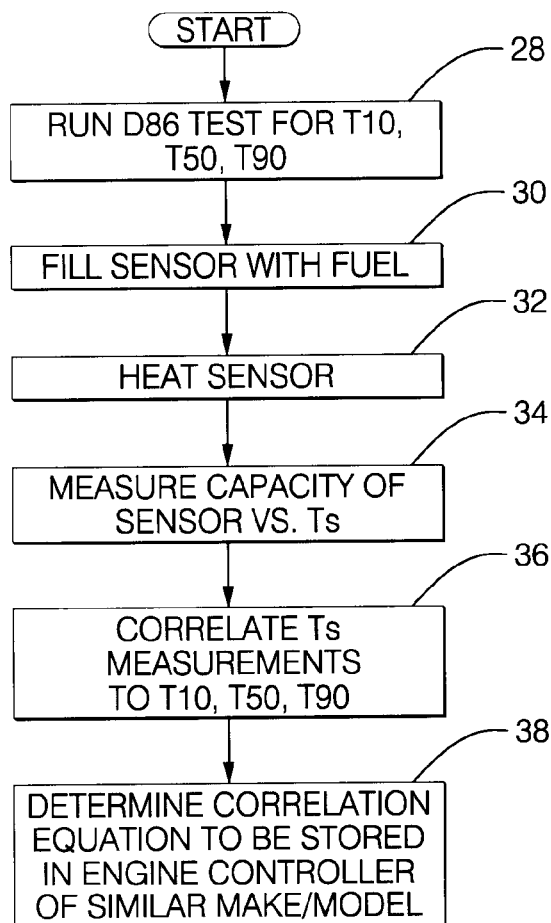
FIG. 2 is a flow chart of the method to correlate measurements from the sensor to the ASTM D86 test.
Figure 3:
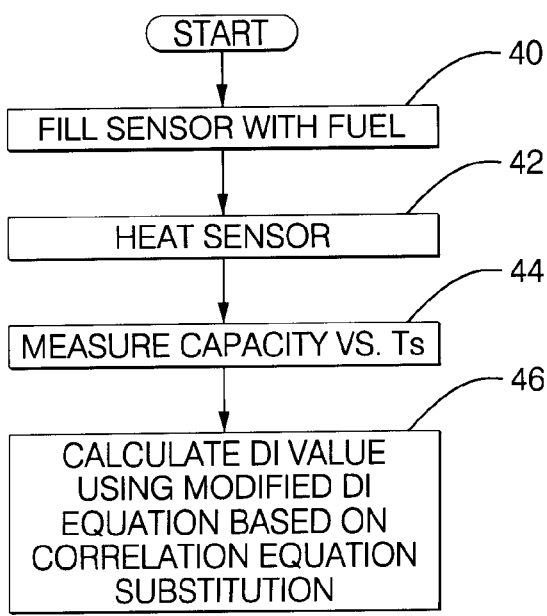
FIG. 3 is a flow chart of the method to calculate the driveability index (DI) number on the vehicle according to the present invention.

The fuel driveability index (DI) is a number corresponding to or representative of fuel volatility. The method used to measure the driveability index (DI) is described in American Society for Testing In Materials (ASTM) test method D86. In this standardized test, a hundred milliliter sample of gasoline is placed in a container. The temperature of the sample is ramped up, causing the gasoline to completely evaporate in approximately 30 minutes. As the evaporation proceeds, the vapors are distilled and collected in a second container. The distilled volume is recorded as a function of the temperature of the heated container. In particular, $T_{10}$ $T_{50}$, $T_{90}$ are the temperatures in degrees Fahrenheit at which 10%, 50%, and 90% of the original volume has been distilled and are the temperatures used to calculate the DI of the gasoline in the equation: $1.5T_{10} + 3T_{50} + T_{90}$.

Referring now to the drawings, according to the invention, a sensor 10 having a sensing element 12 is mounted within the fuel tank 14 of a vehicle and programmed to measure the DI number at each shut-off of the engine. The sensing element 12 is mounted within the fuel tank 14 so that the sensing element 12 is in communication with a flow of gasoline in the fuel line 16 when the engine 18 is running but remains above the maximum fuel level in the tank. When the vehicle engine 18 is stopped, and the fuel drains away from the sensor 10, a known volume of gasoline is drawn into the sensing element 12. The sensing element 12 is connected with a capacitance measuring circuit 20 to represent the volume of fuel in the sensing element 12. A heating element 22 and a temperature measuring circuit 24 are attached to the sensing element 12 to monitor the change in temperature of the sensing element 12 over time.

As the sensing element 12 is heated, the fuel within the sensing element 12 begins to evaporate. The temperature and capacitance of the sensing element 12 are monitored. Output from the capacitance circuit 20 and the temperature measurement circuit 24 are provided to the engine controller 26 to perform the DI calculations.

However, by using an in-line sensor 10 in the vehicle, the initial temperature read by the sensor 10 cannot be controlled, the sample amount is smaller and the measuring time is shorter than in the ASTM D86 test. By reducing the measuring time and sample amount, the $T_{10}$, $T_{50}$, and $T_{90}$ show large differences compared with the ASTM D86 test. Therefore, correlations between the ASTM D86 test and results from the sensing element 12 for a given fuel must be established. Since the ASTM D86 test is the industrial standard, it is necessary to initially calibrate the measured results from the particular model of sensing element 12 selected for the vehicle make and model to match the results obtained from the standard.

Before the sensor 10 is operatively connected to the engine controller of a vehicle, the measurements from the sensor 10 must be calibrated relative to the ASTM D86 test. Calibration can take place in a laboratory environment which simulates the ultimate operating environment of the sensor, or it can take place on a test vehicle that simulates the particular make and model of a vehicle on which identical sensors 10 will ultimately be installed. Thus, a calibration (step 28) includes obtaining a first sample of fuel of known or unknown physical characteristics, and dividing the first sample into two containers wherein a first container contains a first known volume (100 mL) of the first sample from which the DI will be calculated according to the ASTM D86 test described above, and a second container contains a second known volume of the first fuel sample from which DI will be calculated using the sensor 10. The DI value for the fuel contained in the first sample is then calculated using the D86 test procedures which include obtaining values for $T_{10}$, $T_{50}$, and $T_{90}$.

The second container contains a volume of the first sample of fuel and is used to fill the sensing element 12 (step 30). The sensing element 12 has a known volume which depends on the physical characteristics of the particular sensing element 12. The volume of one sensing element used for testing had a range of 0.04–0.1 mL. The fuel contained in the sensing element is heated (step 32) by a controlled heating element 22 with the sensor 10 to provide normalized measured curves (FIG. 4), wherein the normalized output (fuel level) is plotted versus sensor temperature (in degrees Celsius) (step 34).

In the preproduction calibration of the measurements of the sensor 10, a known volume of a fuel sample is placed in the sensing element 12. The known volume is the same amount that will be drawn into the sensing element by the capillary effect on-board the vehicle. Preferably, the heating (step 34) of the sensing element 12 is done in an environment similar to the on-board environment, since tank pressure and the thermal mass of the sensor 10 and its associated brackets can affect the vaporization rate of the fuel. When the heating element 22 is actuated, the fuel is heated and vaporized, i.e. boiled off and volatilized. The fuel quantity and the fuel level in the sensing element 12 decreases as the heating time increases. With controlled heat applied to the sensor 10, the rate of fuel decrease will depend on the volatility, or the driveability index (DI) of the fuel. Monitoring the fuel level at the output of the sensor 10, as a function of the sensor temperature (step 34) will provide values corresponding to a function of the fuel volatility.

Since the sensor 10 is small and the heat is localized within the sensing element 12, the fuel in the sensing element 12 can be emptied at much lower temperatures than the end of boiling point (EBP) measured in the D86 test. For example, a typical measured fuel EBP temperature is 200° C. in the D86 test. The fuel in the sensing element 12 can be emptied at approximately 100° C. Therefore, the sensor measurement can be completed in a reasonable time frame, shorter than three minutes, and be completed at a temperature below 120° C.

As the sensing element 12 is heated, the output of the sensor 10 as a function of sensor temperature provides a normalized curve. The normalized curve defines the measured $T_{xs}$ as a sensor temperature at which x % of the fuel level has been vaporized. From the D86 test, the temperatures, $T_x$ are known, where x equals 10%, 50%, and 90% of the fuel level vaporized. Therefore, a linear equation can be calculated to correlate $T_{xs}$ to $T_x$ for each of the values of x equaling 10%, 50%, and 90% (step 36). For each of the x values of 10%, 50%, and 90% there will be a correlation factor or equation that can be used when an unknown fuel is measured by the sensor 10. The correlation factor or equation is stored in the engine controller 26 of the vehicle (step 38) and will use the measured $T_{10s}$, $T_{50s}$, and $T_{90s}$ to calculate the needed $T_{10}$, $T_{50}$, and $T_{90}$ for the aforementioned driveability index (DI) calculation. The correlation factor or equation can be stored in the engine controller 26 in the form of equations or look up tables, or modified constants for the DI equation.

Hereinafter for illustration purposes only, is an example of the process of calculating the DI number. In a laboratory test, three non-ethanol fuel samples are used to measure the driveability index (DI) calculation by using the D86 method and the sensor measured results. Using the number set representation as DI ($T_{10}$, $T_{50}$, and $T_{90}$), the three samples had properties of 1119 (103, 215, 319), 1230 (127, 235, 334), and 1294 (146, 245, 340) respectively from the D86 method.

Figure 4:
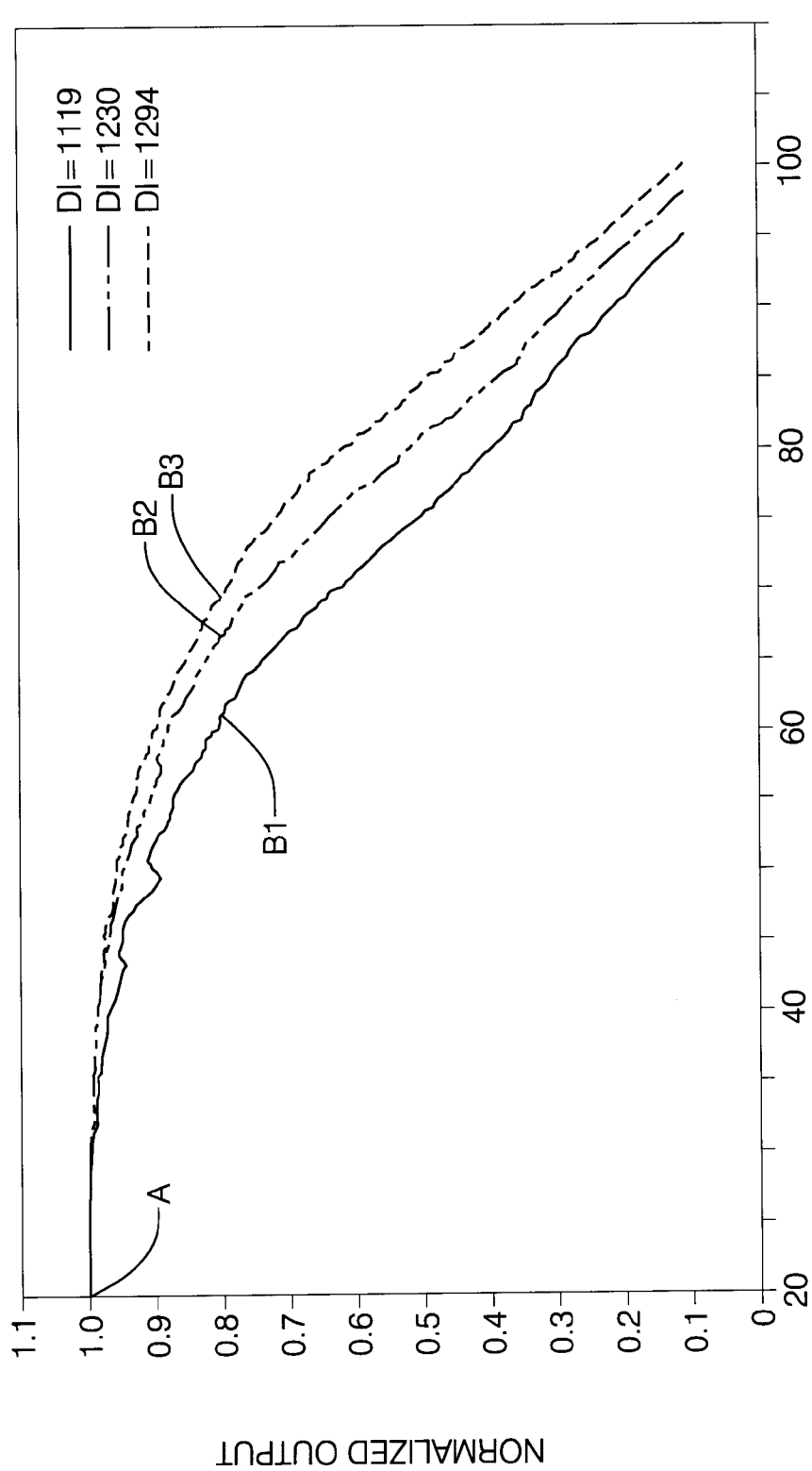
FIG. 4 is a graph of the capacitance of the sensing element vs. the temperature for a tested sensor with three unknown fuels samples.

Samples from the same three non-ethanol fuels are used in the heated sensor test either in a laboratory setting or on the vehicle. Using the number set ($T_{10s}$, $T_{50s}$, and $T_{90s}$) to represent the sensor measured results, testing provides (50, 75.8, 95.4), (55.7, 81.2, 98.4), and (59.4, 85, 100.2) for the fuel samples which had DI of 1119, 1230, and 1294 values respectively. FIG. 4 is a graph illustrating the normalized measured curves of the aforementioned example. Since the sensor temperature is recorded in degrees Celsius as opposed to degrees Fahrenheit used in the D86 test procedure, linear calculations result in the following correlation equations: $T_{10}=4.5436T_{10s}-124.72$; $T_{50}=3.2907T_{50s}-33.784$; and $T_{90}=4.4388T_{90s}-104$.

Using the measured $T_{10s}$, $T_{50s}$, and $T_{90s}$ values and the above correlation equations, the calculated driveability index (DI) numbers for the three fuel samples are 1120, 1226, and 1296 in comparison to the D86 tested numbers 1119, 1230, and 1294, respectively. The differences between the two test methods are −1, 4, and −2, respectively.

Therefore, one method to calculate the fuel DI number on-board the vehicle is to store the correlation factor or equation (step 38) from a previously tested model of sensor 10 having known particular physical characteristics into the engine controller 26 of the vehicle. The fuel in the fuel tank 14 is then tested at predetermined conditions as discussed hereinafter to measure sensor temperature $T_{xs}$ versus x % vaporized output of fuel from the sensor 10 at a specific time. A known volume of fuel from the fuel tank 14 is drawn into the sensing element 12 (step 40). After a short delay period of a few seconds, the heating element 22 is activated to heat the sensing element 12 at a controlled rate (step 42). As the sensing element 22 is heating, the capacitance measuring circuit 20 and the temperature measuring circuit 24 monitors the volume % of fuel vaporized versus the temperature (step 44), in particular, the temperatures ($T_{10s}$, $T_{50s}$, $T_{90s}$) when the volume % of fuel vaporization is 10%, 50% and 90% respectively. The measurement of the $T_{10s}$, $T_{50s}$, and $T_{90s}$ values will be applied to the stored correlation factors or equations to provide the $T_{10}$, $T_{50}$, and $T_{90}$ values used to calculate the DI number (step 46) of any non-ethanol fuel in a vehicle. Alternatively, the measured temperatures can be used in the DI equation after substitution of the correlation equations therein and simplification of the equation. Such as, by way of example and not limitation, the equation: $DI_s = 6.82 T_{10s} + 9.87 T_{50s} + 4.4388 T_{90s} - 392.43$.

As an alternative, it may be necessary or preferable to calculate the DI information in as short of time and as low of a temperature as possible. Terminating the sensor heating at a smaller percentage of vaporized fuel, such as 70% instead of 90%, provides added advantages without significantly diminishing the correlation between the measured data of the sensing element 12 and the standard D86 test. If the sensor 10 is subject to lower temperatures the design of the sensor 10 is simplified. Further, if there is adequate amount of fuel in the sensing element 12 when the test is terminated, solid residue deposits on the sensor 10 are prevented. It is possible to terminate the sensor measurements when at least 50% but less than 90% of the fuel level has been vaporized. In particular, if the test is terminated when 70% of the fuel level has been vaporized, this will provide information of a termination temperature $T_{70s}$. Again using linear analysis, a correlation factor or equation can be calculated to extrapolate the measured $T_{70s}$ to $T_{90}$. The correlation equation can be substituted into the DI equation and the results simplified into a new $DI_s$ equation for use with these operating characteristics.

Using the same example as illustrated above, the correlation equations would remain the same for $T_{10}$ and $T_{50}$. A new correlation equation would replace the previous correlation equation for $T_{90}$. In the above example, the correlation between $T_{70s}$ and $T_{90}$ is: $T_{90} = 3.1305 T_{70s} + 52.173$.

Therefore, in a vehicle using a sensor 10 having the same physical characteristics as the sensor 10 tested in the aforementioned example, correlation equations stored in the engine controller 26 for $T_{10}$ and $T_{50}$ would remain the same, but include instead of the previous correlation equation for $T_{90}$ would have the correlation equation between $T_{70s}$ and $T_{90}$.

In the above example, using the measured $T_{10s}$, $T_{50s}$ and $T_{70s}$ values and aforementioned correlation measurements, the calculated driveability index (DI) numbers for the fuel samples are 1120, 1225, and 1297 in comparison to the D86 test numbers of 1119, 1230, and 1294, respectively. The differences between the calculated DI numbers and the D86 numbers are −1, 5, and −3 respectively. Alternatively, the measured temperatures can be used in the DI equation after substitution of the correlation equations therein and simplification to produce a modified equation, by way of example such as $DI_s = 6.82 T_{10s} + 9.87 T_{50s} + 3.1305 T_{70s} - 236.26$ for the exemplary data being used.

As another alternative, the temperature at which 10% of the fuel level is vaporized can be calculated instead of reading directly from the sensor measurement. In this process, a quadratic equation is used to fit the portion where the normalized output ranges from 0% of the fuel level is vaporized to 20% of the fuel level is vaporized. In the above example, the data of each curve represented in the graph of FIG. 4 between the normalized output 1.0 at A and the normalized output 0.8 at $B_1$, $B_2$, and $B_3$ is fitted with a quadratic equation. The quadratic equation is solved to determine the fitted temperature $T_{10f}$ after 10% of the fuel volume is vaporized. A linear equation is then used to correlate $T_{10f}$ to $T_{10}$. The new calculated $T_{10f}$ value is used in place of the $T_{10s}$ in the correlation equation to calculate $T_{10}$. Using the same data as previously described in the above example and when the quadratic equation is used to fit the data to calculate $T_{10f}$, it is found that there is only a small difference between the fitted $T_{10f}$ and the measured $T_{10s}$. In particular, in the above example the results for $T_{10f}$ are 50.2, 56, and 58.2° C. in comparison to the results for $T_{10s}$ of 50, 55.7, and 59.4° C. respectively. When the correlation measurements are used based on the quadratic equation fitting for $T_{10}$ value, the driveability index numbers are 1122, 1227, and 1289 in comparison to the D86 test results of 1119, 1230, and 1294 respectively. The differences between the two tests procedures are −3, 3, and 5, respectively. Solving for the fitted $T_{10f}$ valve is advantageous in noisy electronic environments where the measured curve is not a clean curve, but includes many fluctuations.

Preferably, the starting of this measurement should follow the fuel loading without a long delay. In particular, it is preferred to initiate the measurement a few seconds after the engine is turned off so that the loading temperature of the fuel into the sensor and starting temperature of the heating are within a small deviation. Further by initiating the measurement after the engine is turned off, a new DI number can be calculated for the next start.

The benefits of calculating a DI number on-board the vehicle includes a decrease in HC and CO emissions while improving fuel economy. Further, costly hardware, such as the AIR pump or the precious metal in the catalytic converter, could be eliminated and be replaced with the low-cost sensor. In addition, new EPA regulations would be easier to meet.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for calculating a fuel driveability index (DI) value on-board a vehicle having a fuel tank and an engine controller, said method comprising the steps of:

providing a sensor in the vehicle in communication with a flow of fuel from the fuel tank, said sensor having a capacity to hold a known volume of fuel;

holding the known volume of fuel from the fuel tank in the sensor;

heated the sensor and volume of fuel therein;

measuring temperatures of the sensor relative to the volume of fuel remaining in the sensor as the sensor is heating; and applying at least some of the measured temperatures to predetermined correlation equations for matching the measured temperatures with measured values from a standardized method of ASTM D86;

calculating a DI value from measured $T_{10}$, $T_{50}$, and $T_{90}$ values and the correlation equations, wherein $T_{10}$ is the temperature when 10% of the fuel in the sensor has been distilled, $T_{50}$ is the temperature when 50% of the fuel in the sensor has been distilled, and $T_{90}$ is the temperature when 90% of the fuel in the sensor has been distilled.

2. The method of claim 1 wherein the step of heating the sensor occurs after the vehicle is turned off.

3. The method of claim 1, wherein the step of measuring temperatures includes the steps of terminating when the volume of fuel in the sensor is less than 90% vaporized and then using linear analysis to extrapolate the $T_{90}$ value.

4. The method of claim 3, wherein the measuring of temperatures terminates at a predetermined percentage of output volume providing a termination temperature is used to calculate the DI value.

5. The method of claim 1, wherein the step of measuring the temperatures includes the steps of:

measuring the temperatures of the sensor when the output volume of the sensor ranges from 0% to 20% vaporization of the fuel volume; and fitting a quadratic equation to the ranges to solve for a $T_{10f}$ value.

6. The method of claim 5, wherein the step of applying at least some of the measured temperatures includes the step of applying the $T_{10f}$ value to at least one of the correlation equations to solve for $T_{10}$.

7. The method of claim 1, wherein the correlation equations are stored in the engine controller.

8. The method of claim 1, further comprising the steps of:

prior to applying at least some of the measured temperatures to correlation equations, running a ASTM test method D86 with a volume of fuel and solving for temperatures $T_{10}$, $T_{50}$, $T_{90}$, when the volume % of the fuel vaporized is 10%, 50% and 90% respectively;

heating a related other sensor with the same known volume of the fuel therein as the sensor;

measuring for related sensor temperatures relative to the % volume of fuel vaporized from the related sensor; and correlating predetermined measured related sensor temperatures to the temperatures, $T_{10}$, $T_{50}$, and $T_{90}$ from the ASTM test method D86 to provide the correlation equations.

9. The method of claim 8, further comprising the step of:

storing said correlation equations into the engine controller.

10. The method of claim 1, further comprising the step of storing a modified DI equation in the engine controller.

11. A system for calculating a fuel driveability (DI) value on-board a vehicle having a fuel tank and an engine controller, the system comprising:

means for holding a known volume of fuel from the fuel tank in a sensor, said sensor in communication with a flow of fuel from the fuel tank;

means for heating the sensor and the volume of fuel therein;

means for measuring temperatures of the sensor relative to the volume of fuel remaining in the sensor as the sensor is heated, and means for calculating a DI value from measured $T_{10}$, $T_{50}$ and $T_{90}$ values and predetermined correlation equations for matching the measured temperatures with measured values from a standardized method of ASTM D86, wherein $T_{10}$ is the temperature when 10% of the fuel in the sensor has been distilled, $T_{50}$ is the temperature when 50% of the fuel in the sensor has been distilled, and $T_{90}$ is the temperature when 90% of the fuel in the sensor has been distilled.

12. The system of claim 11, wherein the sensor is positioned in the fuel tank.

13. The system of claim 11, wherein means for calculating a DI value includes a modified DI equation stored in the engine controller.

14. A system for calculating a fuel driveability (DI) value for a vehicle having a fuel tank, the system comprising:

means for calculating a DI value from a standard test and a first sensor having a known volume of fuel therein by measuring the volume of fuel versus temperature as the fuel is heated;

a related sensor having the capacity for storing another sample of the same known volume of fuel as the first sensor wherein said related sensor is located in the vehicle and in fluid communication with fuel flow from the fuel tank;

means for heating the related sensor and the volume of fuel therein;

means for measuring the volume of fuel in the related sensor versus the temperature of the sample fuel; and means for correlating the measured temperature and volume of fuel in the related sensor with the measured temperature and volume of fuel in the first sensor to provide correlation equations for calculating the DI value from the related sensor.

\* \* \* \* \*